US00PP32212P2

(12) United States Plant Patent
Bak et al.

(10) Patent No.: US PP32,212 P2
(45) Date of Patent: Sep. 15, 2020

(54) ***VRIESEA* PLANT NAMED 'BRIGHT DAY'**

(50) Latin Name: ***Vriesea* sp.**
Varietal Denomination: BRIGHT DAY

(71) Applicant: Corn Bak B.V., Assendelft (NL)

(72) Inventors: Elly Bak, Rijsenhout (NL); Nicolaas Steur, Oude Niedorp (NL)

(73) Assignee: Corn Bak B.V. (NL)

( * ) Notice: Subject to any disclaimer, the term of this patent is extended or adjusted under 35 U.S.C. 154(b) by 0 days.

(21) Appl. No.: 16/602,005

(22) Filed: Jul. 18, 2019

(51) Int. Cl.
*A01H 5/02* (2018.01)
*A01H 6/22* (2018.01)

(52) U.S. Cl.
USPC ..... Plt./370

(58) Field of Classification Search
USPC ..... Plt./263.1, 370
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Vriesea* plant named 'BRIGHT DAY' characterized as a funnel form rosette plant, measuring about 38 cm in height (when flowering) and 45 cm in diameter, producing compound, red in color (RHS 45B), bipinnate spike inflorescence, measuring about 20 cm in height and about 18 cm in diameter, about 7 branches, and yellow-green foliage, measuring about 25-30 cm in length and about 3.5 cm to 4.5 cm in width.

1 Drawing Sheet

Latin name of the genus and species: *Vriesea* sp.
Variety denomination: 'BRIGHT DAY'.

BACKGROUND OF THE INVENTION

The present invention relates to a new and distinct cultivar of *Vriesea* plant, botanically known as *Vriesea* sp., hereinafter referred to by the cultivar name 'BRIGHT DAY'. The genus of *Vriesea* belongs to the Bromeliaceae family. The new *Vriesea* cultivar is a product of a planned breeding program conducted by the inventors, Elly Bak and Nico D. M. Steur, in Assendelft, The Netherlands. The objective of the breeding program is to develop a new *Vriesea* variety with good growing habit and attractive inflorescence.

The new *Vriesea* cultivar 'BRIGHT DAY' originated from a cross-made in a controlled breeding program by the inventors in 1999 in Assendelft, The Netherlands. The seed parent is an unpatented *Vriesea* selection designated '910209'. The pollen parent is an unpatented *Vriesea* selection designated '99051414'. 'BRIGHT DAY' was discovered and selected by the inventors in December 2004, as a single flowering plant within the progeny of the stated cross in a controlled environment in Assendelft, The Netherlands.

Asexual reproduction of the new cultivar 'BRIGHT DAY' performed by vegetative means by tissue culture was first performed in 2010, in Assendelft, The Netherlands. The first 'BRIGHT DAY' plants propagated through the use of tissue culture flowered in 2012, in Assendelft, The Netherlands, and have demonstrated that the combination of characteristics as herein disclosed for the new cultivar are firmly fixed and retained through successive generations of asexual reproduction. The new cultivar reproduces true-to-type.

SUMMARY OF THE INVENTION

The cultivar 'BRIGHT DAY' has not been observed under all possible environmental conditions. The phenotype may vary somewhat with variations in environment such as temperature, day length, and light intensity, without, however, any variance in genotype.

BRIEF DESCRIPTION OF THE INVENTION

The following traits have been repeatedly observed and are determined to be the unique characteristics of 'BRIGHT DAY'. These characteristics in combination distinguish 'BRIGHT DAY' as a new and distinct *Vriesea* cultivar:

1. Funnel form rosette.
2. Red bipinnate spike inflorescence.
3. About 7 inflorescence branches.
4. Yellow green foliage.

PARENT COMPARISON

Plants of the parents, '910209' and '99051414' are no longer available to provide a botanical comparison with the new *Vriesea* cultivar 'BRIGHT DAY'.

COMMERCIAL COMPARISON

'BRIGHT DAY' is similar in most horticultural characteristics to the unpatented commercial variety *Vriesea* 'Stream', U.S. Plant Pat. No. 18,227. However, the new variety, 'BRIGHT DAY' differs in the following:

1. The new variety has more inflorescence branches than this comparator. 'Bright Day' produces on average 7 inflorescence branches. 'Stream' produces on average 4.
2. The new variety has longer leaves than this comparator. 'Bright Day' produces foliage 25 to 30 cm long on average, 'Stream' produces foliage 15 to 25 cm on average.

BRIEF DESCRIPTION OF THE PHOTOGRAPH

The accompanying drawing illustrates the overall appearance of the new *Vriesea* cultivar 'BRIGHT DAY' showing the colors as true as is reasonably possible with colored reproductions of this type. Colors in the photograph may differ slightly from the color values cited in the detailed botanical description which accurately describes the color of 'BRIGHT DAY'.

The photograph shows a side perspective view of a typical potted flowering plant of 'BRIGHT DAY' at about 18 months of age from potting size.

DETAILED BOTANICAL DESCRIPTION

'BRIGHT DAY' has not been observed under all possible environmental conditions. The phenotype of the new cultivar may vary with variations in environment such as temperature, light intensity, day length, fertilizers and humidity without any change in the genotype of the plant. The afore mentioned photograph, together with the following observations, measurements and values describe the new *Vriesea* cultivar as grown in a greenhouse in Assendelft, The Netherlands, under conditions which closely approximate those generally used in commercial practice. Plants of 'BRIGHT DAY' were grown in a greenhouse with day temperatures ranging from 20° C. to 28° C. and night temperatures ranging from 18° C. to 23° C. No artificial lighting or photoperiodic treatments were conducted, but plants of 'BRIGHT DAY' are forced into flowering. The following fertilizer is added when growing plants of 'BRIGHT DAY': 1 part nitrogen, 0.6 parts phosphor, 2 parts Kalium and 0.1 parts magnesium. Color references are made to The Royal Horticultural Society Colour Chart (RHS) 2007, except where general colors of ordinary significance are used. Color values were taken under daylight conditions in a greenhouse in Assendelft, The Netherlands. The age of the plants of 'BRIGHT DAY' described is about 18 months from potting size.

Botanical classification: *Vriesea* 'BRIGHT DAY'.

PROPAGATION

Type of propagation typically used: Tissue culture.

PLANT

Growth habit: Funnel form rosette.
Height: Approximately: 38 cm.
Plant spread: Approximately: 45 cm.
Plant vigor: Good.
Flowering season: A fully grown plant can flower year-round, starting approximately 16 weeks after induction of natural light or trough flowering treatment.
Cold tolerance: Frost tender. Temperatures below 5° C. may damage plants.
Fragrance: None.
Root description: Densely branched, non-fibrous, non-fleshy, colored Greyed-orange; near RHS 165A.

FOLIAGE

Leaf:
- *Quantity.*—About 26.
- *Average length.*—25-30 cm.
- *Average width.*—3.5-4.5 cm.
- *Shape of blade.*—Broad and linear.
- *Apex.*—Abruptly acuminate.
- *Base.*—Strap-like around central axis.
- *Margin.*—Entire.
- *Texture of top surface.*—Smooth, glabrous.
- *Texture of bottom surface.*—Smooth, glabrous.
- *Color.*—Young foliage upper side: RHS Yellow-Green 147A. Young foliage under side: RHS Yellow-Green 147A. Mature foliage upper side: RHS Yellow-Green 147A. Mature foliage under side: RHS Yellow-Green 147A.
- *Venation.*—Type: Parallel. Venation coloration: Indistinguishable from leaf blade.

Petiole: No petiole present.

INFLORESCENCE

General description: 1 flower per floral bract, typical for the genus *Vriesea*; flowering is normally in progression from base to tip of scape.
- *Inflorescence height.*—Approximately 27 cm.
- *Inflorescence width.*—Approximately 13 cm.
- *Shape.*—Bipinnate spike (main spike about 15 cm in length and about 4 cm in width, side spike about 14-20 cm in length and about 4 cm in width). Typically 7 branches.
- *Color.*—RHS Red 45B.

Corolla:
- *Form.*—Long and narrow, petals and sepals fused at the base around the ovary.

Petals:
- *Number.*—3 per flower.
- *Length.*—About 4.7 cm.
- *Width.*—About 0.8 cm.
- *Overall shape.*—Ligulate.
- *Apex shape.*—Obtuse.
- *Base shape.*—Fused.
- *Texture.*—Smooth.
- *Color.*—Upper surface: RHS Yellow 7C, Yellow-Green 144B at tip. Lower surface: RHS Yellow 7C, Greyed-Orange 164B at tip.

Sepals:
- *Number.*—3 per flower.
- *Length.*—About 2.5 cm.
- *Width.*—About 0.7 cm.
- *Overall shape.*—Ligulate.
- *Apex shape.*—Acute.
- *Base shape.*—Fused.
- *Texture.*—Smooth.
- *Color.*—Translucent, yellow with red flush, closest to RHS Yellow 8C and Red 43C.

REPRODUCTIVE ORGANS

Androecium:
- *Stamen.*—Number: 6 per flower. Length: About 4 cm. Diameter: About 0.1 cm. Color: RHS Yellow 8C.
- *Anther.*—Length: About 0.6 cm. Color: RHS Yellow 8D.
- *Pollen.*—Amount: Numerous. Color: Yellow, too small to accurate measure with RHS chart.

Gynoecium:
- *Pistil.*—Number: 1 per flower. Length: About 5.5 cm.
- *Stigma.*—Shape: 3-parted. Width: About 0.3 cm. Color: RHS Yellow-Green 151C.
- *Style.*—Length: About 5 cm. Color: RHS Yellow 8C.

*Ovary.*—Shape: Conical. Length: About 0.4 cm. Diameter: About 0.2 cm. Color: RHS Yellow 8D.

OTHER CHARACTERISTICS

Disease resistance: Neither resistance nor susceptibility to the normal diseases and pests of *Vriesea* has been observed.

Temperature tolerance: Frost tender. Temperatures below 5° C. may damage plants.

Fruit/seed production: No fruits/seeds detected to date.

What is claimed is:

1. A new and distinct cultivar of *Vriesea* plant named 'BRIGHT DAY' as herein illustrated and described.

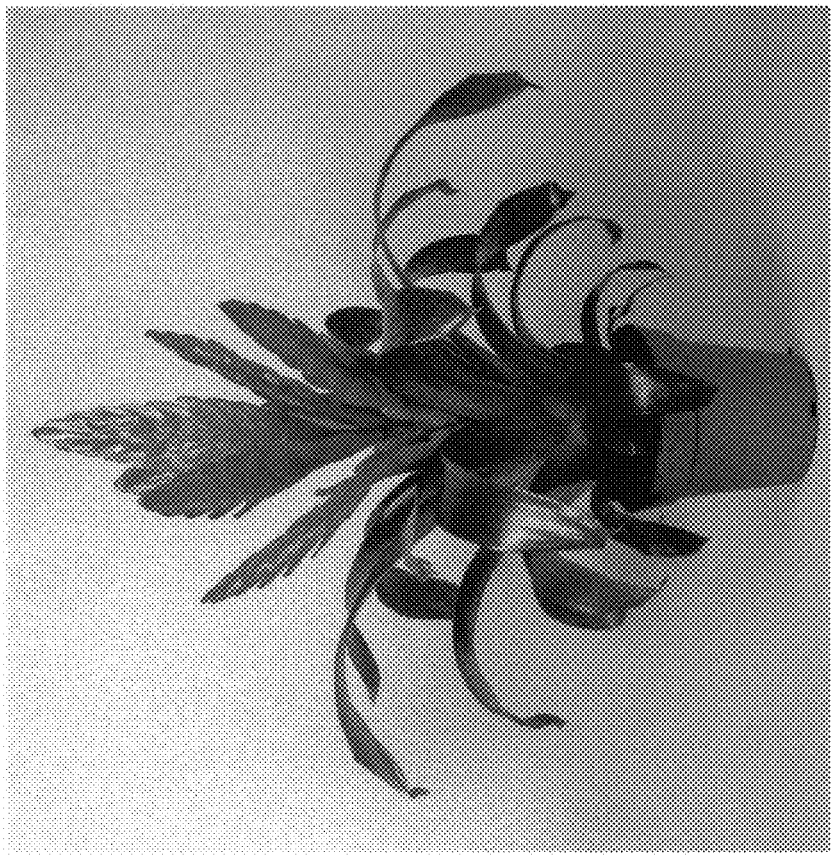

* * * * *